United States Patent [19]
Alcorn et al.

[11] 3,962,140
[45] June 8, 1976

[54] NICKEL-COPPER-MOLYBDENUM METHANATION CATALYST

[75] Inventors: William R. Alcorn, Rocky River; Leonard A. Cullo, Solon, both of Ohio

[73] Assignee: The Harshaw Chemical Company, Cleveland, Ohio

[22] Filed: Mar. 10, 1975

[21] Appl. No.: 556,808

[52] U.S. Cl. .............................. 252/470; 252/465; 260/449 M
[51] Int. Cl.$^2$ ......................................... B01J 23/84
[58] Field of Search ......................... 252/465, 470; 260/449 M

[56] References Cited
UNITED STATES PATENTS
3,854,895   12/1974   Muller ............................ 260/449 M

*Primary Examiner*—W. J. Shine
*Attorney, Agent, or Firm*—Alfred D. Lobo; James A. Lucas

[57] ABSTRACT

A supported methanation catalyst and a process for utilizing the catalyst are disclosed. The catalyst yields a product containing a major proportion of methane and some ethane. Methanation of a gaseous feed stream containing from about 10 to about 50 mole percent carbon monoxide, and from about 1.0 to about 3.0 times as much hydrogen as carbon monoxide, is effected at elevated temperature and high pressure continuously over a prolonged period of time, while a conversion of carbon monoxide in excess of 80 mole percent is maintained. Thermal stability at elevated temperature and pressure permits essentially continuous use of the catalyst for extended periods of time without time-consuming shutdowns. High conversion of gaseous feed and thermal stability of catalyst permits economical process design which utilizes a minimal recycle, if any.

The supported catalyst consists essentially of a complex of oxides of nickel, copper and molybdenum which complex is reduced on the support prior to or during use. The complex of oxides consists of from about 5 to about 20 percent by weight molybdenum oxide, and from about 5 to about 40 percent by weight nickel oxide, each amount based on total catalyst, present in a weight ratio of nickel oxide to copper oxide in the range from 1:1 to about 9:1, and preferably in the range from about 1 to about 3.

3 Claims, No Drawings

NICKEL-COPPER-MOLYBDENUM METHANATION CATALYST

BACKGROUND OF THE INVENTION

This invention relates to an improved methanation catalyst and method for producing methane from carbon monoxide and hydrogen. The catalyst is termed a methanation catalyst because the major component of the reaction product, on a moisture-free basis, is methane. More specifically, this invention relates to a methanation catalyst and its use in a method of converting a gaseous feed containing the reactants hydrogen and carbon monoxide present in a molar ratio of about three to one, generally in the presence of methane and minor amounts of other gases such as nitrogen, carbon dioxide, steam, and the like, into a gaseous product stream containing a major proportion of methane, disregarding water. The catalyst is formed by reducing a complex of the combined oxides of nickel, copper and molybdenum supported on a catalyst support, the relative ratios of nickel, copper and molybdenum being defined within relatively narrow limits for preferred operation.

The prior art is replete with numerous metallic catalysts which have been utilized, both in supported and non-supported form, to catalyze the reaction of carbon monoxide and hydrogen. In general, though some methane is formed with prior art metallic catalysts, most are directed to the standard Fischer-Tropsch reaction for the synthesis of hydrocarbons starting with carbon monoxide and hydrogen, and therefore are specifically directed to the formation of hydrocarbons of relatively high molecular weight.

Though the methanation of carbon monoxide has been referred to in numerous references, including those which teach the Fischer-Tropsch synthesis, it is only in the face of declining gas reserves that a great deal of attention has been focused on arriving at a practical and economical process for methanation of feed streams containing high CO content, and of course, a catalyst which will fulfill the demanding requirements of such a process. The large number of catalytic elements disclosed in the prior art are of little help with respect to obtaining a commercially significant catalyst to upgrade less accessible energy sources such as coal to methane, which catalyst will help stem the shortage of natural gas as a vital energy source. It will be apparent from disclosures of prior art Fischer-Tropsch catalysts that the formation of methane in any substantial amount is regarded as detrimental to the catalyst's performance. Preferred catalysts are those which yield higher hydrocarbons, preferably containing in excess of three carbon atoms. Disclosures with respect to the Fischer-Tropsch synthesis catalyst are so all-encompassing as to cover combinations of almost any metallic element in the periodic table. The disclosures of Fischer-Tropsch catalysts which might suggest the reduced oxides of nickel, copper and molybdenum equally suggest innumerable other combinations as essential catalytic ingredients. Moreover, the proportions of components specifically suggested for prior art commercial methanation catalysts are found to be generally unsuited for commercial methanation at elevated pressures in excess of about 500 psi, and where carbon monoxide is present in excess of about 10 percent of the feed, because of their instability under intense exothermic heats of reaction generated under those conditions.

Several processes are currently being developed for coal gasification. All the processes require final methanation of a mixture including $H_2$ and CO to yield a pipeline quality product.

The catalyst of the instant invention, and the method for using it, are especially directed to large scale industrial operations where large amounts of carbon monoxide and hydrogen, at a pressure in excess of 300 psig., are to be continuously and reliably converted primarily to methane and water. More specifically, the instant catalyst and the method for using it are directed to the conversion of gaseous products obtained by the gasification of coal, or from offgases from the retorting of oil shale or the liquefaction of coal, or the gasification of heavy petroleum residues, and the like, all of which are characterized by producing carbon monoxide-rich gas, usually in the presence of large quantities of hydrogen. The gases so produced have a low heating value, that is, less than 500 Btu. per standard cubic foot of gas, and contain minor amounts of other gases, particularly methane, carbon dioxide, nitrogen oxides, and the like. Since the methanation reaction is strongly exothermic it is essential that the catalyst be thermally stable. Also, since efficient recovery of the heat generated in the methanation reaction is a significant factor in the overall efficiency of the process it is desirable to carry out the methanation reaction at as high a temperature as possible.

Since it is necessary to supply pipeline gas at high pressure it is desirable to conduct a methanation reaction at elevated pressure in the range from about 300 psig. to about 1500 psig. Though high pressure reaction conditions benefit both the rate and equilibrium of the methanation reaction, the effect on the methanation catalyst is to increase the severity of the methanation reaction and to subject the catalyst to a high heat release in the reaction zone.

Numerous references which teach methanation with nickel catalysts illustrate the problems set forth hereinabove. The problem of thermal degradation of the catalyst has been attacked by process and equipment design modifications which tend to increase cost and decrease efficiency of the process. For example, several well-regarded processes use a recycle gas to dilute the feed to the methanator so as to maintain the CO concentration below 10% and usually below 5%. Another well-regarded process utilizes heat-transfer surfaces coated with catalyst in order to control the exothermic heat.

Prior art synthesis catalysts, for instance Fischer-Tropsch catalysts, are deliberately selected and the processes are operated to minimize the formation of $CH_4$ and to maximize the yield of higher molecular weight products. Other synthesis catalysts are disclosed to contain the transition elements of groups VB, VIB and VIII promoted with still other elements, thus teaching that almost any combination of elements in a large number of Groups will provide an effective synthesis catalyst. With respect to methanation catalysts it is stated:

The Group VIII transition elements Fe, Co, Ni, Ru, Rh, Pd, Os, Ir, and Pt, particularly the former three, have been found to be effective methanation catalysts.

The problem areas in catalytic methanation are generally agreed to be associated with the strong exothermicity of the reaction which can cause excessive temperature and catalyst deactivation by sintering, carbon deposition and sulfur poisoning of the catalyst. (See "Catalysts for Coal Conversion", by John L. Cox, *Symposium on Clean Fuels from Coal*, IGT, Chicago (September 1973) pp. 311–340.

We know of nothing in the prior art which teaches that the supported combined oxides of nickel, copper, and molybdenum, activated by reduction on the support, will provide an effective methanation catalyst characterized by an insensitivity to high concentrations of carbon monoxide at pressures in excess of 500 psi, thermal stability at an operating temperature in the range from about 400°C to about 625°C, and a satisfactory conversion of carbon monoxide.

It should be noted that methanation reactions have been employed in the clean-up of reformer product gases prior to their introduction into fuel cells, and for the removal of carbon monoxide from the feed to reactors in ammonia synthesis plants. Most such methanation catalysts are primarily nickel-based and include no copper, are not suitable for converting CO which is present in excess of about ten percent, are easily poisoned or rendered inactive, and therefore have no utility in the particular methanation process of this invention. This is acknowledged in the statement:

Catalytic methanation has been known for 70 years and has been utilized extensively in removing small amounts of CO from hydrogen-containing gases . . . The composition of a typical catalyst is 77% Ni and 22% $Al_2O_3$. It is easily poisoned by sulfur and also rendered inactive by carbon deposition and by sintering.

A variety of reaction systems has been used to overcome the severe problems of the high heat release. (See "Future Catalytic Requirements for Synthetic Energy Fuels", by G. Alex Mills, ACS Meeting, Boston (April 1972); Div. of Fuel Chemistry Preprints, Vol. 16, No. 2, pp. 107–123.

It should also be noted that prior art synthesis catalysts generally utilize the product of a reforming operation in which methane was first converted to carbon monoxide and hydrogen. The carbon monoxide and hydrogen is then utilized to synthesize higher molecular weight products, and not methane. A typical reference in this art is U.S. Pat. No. 2,500,516 to Carpenter, wherein it is disclosed that a catalyst for the synthesis step may be metallic iron, cobalt, or nickel, either alone or on a suitable carrier such as kieselguhr, silica gel, alumina, etc., and including one or more promoter oxides such as the oxides of magnesium, chromium, manganese, aluminum, copper, etc. (Column 6, lines 50–55).

It has long been known that nickel is a highly active methanation catalyst; and also, that molybdenum is a methanation catalyst which has excellent thermal stability and long life, but substantially lower activity than nickel, and poorer selectivity for methane. It is also known that the reduced combined oxides of nickel and molybdenum are initially active, but rapidly obtain the characteristics of reduced molybdenum oxides alone. Reduced molybdenum oxides, with or without a support, are insufficiently selective for the production of methane and are therefore of minimal interest. It is further known that nickel containing a small amount of copper initially provides high conversions of carbon dioxide to methane but a concentration of copper approaching four percent of combined nickel and copper rapidly erodes the activity of the catalyst (see "Nickel, etc., Catalysts for the Hydrogenation of Carbon Dioxide", by L. E. Cratty, Jr., and W. W. Russell, Journal of Am. Chem. Soc., Feb. 20, 1958, Vol. 80, p. 767). Since it is generally accepted that the behavior of a catalyst in the methanation of carbon dioxide is indicative of its behavior in the methanation of carbon monoxide, it is quite unexpected that when copper in excess of four percent is combined with nickel and molybdenum, a thermally stable, active methanation catalyst would result which is effective even at ratios of hydrogen to carbon monoxide which are substantially lower than 3 and as low as 1.

The thermal stability, high activity and ratio flexiblity of our catalyst are also unexpected in light of the recent observations confirming the finding of Sabatier and Senderens that ". . . cobalt also promoted the reaction but that copper, iron, platinum and palladium did not form active catalysts," and further stating that "Thus, by 1925 all of the metals now considered active for methanation of carbon oxides had been identified. In terms of metals important for methanation, the list could now be shortened to Ru, Ni, Co, Fe and Mo." (see "Catalytic Methanation" by G. A. Mills and F. W. Steffgen in *Catalysis Reviews*, Vol. 8(2), pg. 159–210, 1973).

Also known is a gas equilibration catalyst prepared by co-precipitating nickel, aluminum, copper or zinc and chromium as hydroxides, carbonates or basic carbonates, which on calcination in the presence of oxygen or air, form mixed oxides. The co-precipitated metal hydroxides are impregnated with a barium salt that is decomposed to barium oxide by the calcination. Such a catalyst is disclosed in U.S. Pat. No. 3,444,099 to Taylor et al. as being effective to convert exhaust gases from automobiles at a temperature of 485°C and a space velocity of 10,000 volumes of gas at S.T.P. per volume of catalyst per hour. This catalyst includes barium oxide or a metal oxides type promoter such as potassium, cesium, strontium, and the like. Specifically, the reference includes examples of a catalyst containing nickel, molybdenum, copper, chromium, aluminum and barium in which chromium oxide and barium oxide are necessary components. The catalysts (I and K in Table I) convert relatively low percentages of carbon monoxide after short periods of operation. Moreover, there is no reason to conclude that the catalysts which are suitable for low conversion to methane at low CO concentration might also be suitable, with certain modifications, for high conversion to methane at relatively high CO concentration. In particular, there is no suggestion in the art as to how these catalysts may be modified to provide a per pass conversion in excess of 80 percent of carbon monoxide present in a feed containing in excess of 5% CO. Note also, that the disclosure is for the use of the catalyst in the presence of large quantities of normal butane and butylenes.

From the foregoing it will be apparent that much effort has been expended on the development of an effective gas equilibration catalyst wherein the product contains a major amount of methane. Specifically, applicants know of no gas equilibration catalyst for carbon monoxide present in excess of 5% in a substantially olefin-free feed, having the specific combination of the reduced oxides of nickel, copper, and molybdenum as its essential catalytic ingredients on a suitable support, to the substantial exclusion of all other catalytic ingredients. The catalyst of this invention and the method of its use provides a practical and economical process which profers a solution to the burgeoning problem of a dwindling supply of natural pipeline gas, a profitable utilization of industrial off-gases containing large amounts of carbon monoxide and hydrogen, and specifically, a commercially viable scheme for utilizing the gasification of coal.

SUMMARY OF THE INVENTION

It has been discovered that reduced combined oxides of nickel, copper and molybdenum, supported on a catalyst support, provide a unique and surprisingly effective catalyst for the production of methane.

It is therefore a general object of this invention to provide a methanation catalyst for a gaseous feed characterized by its ability to yield a predominantly methane-containing product, on a moisture-free basis, and some ethane, which catalyst has as its essential catalytic ingredients the reduced combined oxides of nickel, copper and molybdenum. The gaseous feed comprises carbon monoxide and hydrogen reactants, or alternatively, a methane-yielding compound such as methanol.

It is another general object of this invention to provide a thermally stable supported catalyst for the commercial production of methane utilizing a feed with a molar ratio of $H_2/CO$ in a wide range of ratios as low as about 1.0 and as high as 10 but preferably about 3.0. This ratio flexibility of the catalyst is especially desirable because the capacity of the catalyst to produce methane as the predominant component of the reaction product, on a water-free basis, is not decreased.

It is still another general object of this invention to provide a supported activated catalytic complex of nickel, copper and molybdenum in a methanation catalyst which maintains a high activity, in excess of 80 mole percent per pass conversion of carbon monoxide in the feed, over extended periods of time, at a reaction zone temperature in the range from about 400° C to about 625°C and a pressure in the range from about 300 psig to about 1500 psig.

It is a specific object of this invention to provide a supported methanation catalyst of sufficient activity and thermal stability as to require little or no recycle for its protection.

It is also a specific object of this invention to provide an activated or reduced catalytic oxide complex obtained by reduction of a catalytic oxide complex defined by the formula

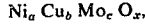

$Ni_a Cu_b Mo_c O_x,$ wherein $a$, $b$ and $c$ are numbers so chosen that when $b$ is unity, $a$ and $c$ are in the range from about 1 to about 9, and preferably in the range from about 1 to about 3, and $x$ is a number determined by the valence requirements of the other elements present.

It is a further specific object of this invention to provide a supported methanation catalyst which consists essentially of a reduced complex of oxides of nickel, copper and molybdenum, wherein the molybdenum oxide is in the range from about 5 to about 20 percent by weight of the catalyst, the nickel oxide is in the range from about 5 to about 40 percent by weight of the catalyst, and the weight ratio of nickel oxide to copper oxide is in the range from about 1 to about 9, and more preferably from about 1 to about 3.

It is another specific object of this invention to provide an activated or reduced catalytic complex of the essential elements nickel, copper, and molybdenum, supported on a conventional catalyst support, wherein the complex is formed by impregnating the support with a molybdenum compound, followed by calcination to yield supported molybdenum oxide, again impregnating the supported molybdenum oxide with a mixture of nickel and copper compounds, again followed by calcination to yield a supported oxide complex of nickel, copper and molybdenum, and thereafter reducing the supported oxide complex to form the activated or reduced catalytic complex.

A process has also been discovered comprising contacting approximately stoichiometrically required amounts of carbon monoxide and hydrogen in a gaseous, substantially olefin-free feed containing in excess of five percent carbon monoxide, over a methanation catalyst consisting essentially of a supported activated catalytic complex of nickel, copper and molybdenum, at a temperature from about 400°C to about 625°C and pressure from about 300 psig to about 1500 psig, in a reaction zone from which the effluent contains a major proportion of methane, on a moisture-free basis, and some ethane, formed by a per pass conversion of at least 80 mole percent of the carbon monoxide fed to the reaction zone.

It is therefore a general object of this invention to provide a process for the conversion of carbon monoxide to methane and a small amount of ethane, comprising contacting carbon monoxide with hydrogen in a predetermined molar ratio of $H_2:CO$ in the range from about 1 mole $H_2$ to about 10 moles $H_2$ per mole CO, in the presence of a methanation catalyst consisting essentially of the reduced combined oxides of nickel, copper, and molybdenum in a reaction zone maintained at from about 400°C to about 625°C and at from about 300 psig. to about 1500 psig., with a contact time from about 0.1 second to 10 seconds, to yield a gaseous product having in excess of 50 percent methane and less than 10 mole percent ethane, based on water-free product gas volume, which gaseous product is produced in excess of 80 mole percent per pass conversion of carbon monoxide fed to the reaction zone, and recovering the methane and ethane.

It is a specific object of this invention to provide a methanation process comprising contacting CO and $H_2$ in approximately stoichiometric amounts with a methanation catalyst which yields a reaction product from which a fuel gas may be recovered containing more than about 90% $CH_4$, about 5% $C_2H_6$, and trace quantities of $C_3H_8$ to the exclusion of paraffins having more than 3 carbon atoms.

These and other objects and advantages of this invention will become apparent to those skilled in the art from the following description of preferred forms thereof and the illustrative examples set forth herein.

DETAILED DESCRIPTION OF PREFERRED EMBODIMENTS OF THE INVENTION

The supported nickel, copper, molybdenum catalytic complex disclosed herein as a gaseous equilibration catalyst is referred to as a supported activated catalytic complex, by which is meant that a mixture of the combined metal oxides is reduced on the catalyst support by any conventional means, such as passing a reducing gas, for example, hydrogen or a mixture of hydrogen and carbon monoxide, over the supported oxide complex, thus activating the oxide complex by reduction to form the activated complex. This is not to be construed as meaning the catalyst is composed entirely of the elements nickel, copper, and molybdenum, as some oxides of the elements may be present even after reduction. Additionally, minor amounts of other elements are generally present as impurities in the commercial production of the catalyst. The presence of such minor amounts of other elements do not contribute a substantial improvement of the claimed catalyst, and in fact, impurities are more likely to erode its especial properties. The proportion of nickel, copper and molybdenum in the catalyst may vary in the ranges described hereinafter, but it will be apparent that the preferred composition of the catalyst is in a relatively narrow range.

The unsupported catalyst of the instant invention presently has limited usefulness on a commercial scale. The continued high conversions with thermal stability while displaying high selectivity over long periods of time, can presently only be obtained utilizing a suitable catalyst support. By catalyst support we refer to any inert carrier which may serve either as a diluent for particles of the catalytic complex of essential ingredients, or upon which carrier the catalytic complex is impregnated or otherwise deposited. Moreover, to obtain best results, it is essential that the oxide complex be activated by reduction while supported on the catalyst support. In a commercial reaction, for economic reasons, it is generally desirable to use a catalyst support which may constitute from 50 percent to 99 percent, and preferably between 70 and 95 percent by weight of the finished catalyst. Any known catalyst support such as alumina, pumice, silicon carbide, zirconia, titania, silica, aluminum-silica, and inorganic phosphates, silicates, aluminates, borates, and carbonates stable under the reaction conditions may be used. The preferred catalyst support is extruded porous gamma-alumina having a surface area of about 180 m$^2$/g., a pore volume in the range from about 0.54 to about 0.61 cc/g., a packed density of about 0.64 g/cc and a Hg density of about 1.09 g/cc.

In the preparation of the methanation catalyst of this invention, the metal oxides can be blended together or can be formed separately, then blended, or, formed separately or together in situ. For example, a molybdenum salt may be mixed with a catalyst support such as gamma-alumina and extruded, granulated or pelleted into small shapes which may then be impregnated with nickel and copper salts prior to calcination and reduction. The metal oxides are generally obtained by calcination of salts which yield the oxides.

A preferred manner of forming the catalytic oxide complex is by first impregnating the catalyst support with a molybdenum salt that is decomposed to molybdenum oxide, which is interspersed in and on the catalyst support, by calcination. Typically, this is done by using ammonium molybdate, or any other water-soluble molybdenum salt, by impregnation with an aqueous solution of the salt in a desired concentration for a preselected period of time, so as to deposit the desired amount of molybdenum on the support. Alternatively, any molybdenum oxide such as the dioxide, trioxide, pentoxide, or sesquioxide may be used; preferred is a hydrolyzable or decomposable molybdenum salt such as a molybdenum halide. A more preferred easily available starting material is ammonium heptamolybdate.

Nickel and copper are thereafter introduced into the catalyst as an oxide or as any salt which upon calcination will yield the oxide. Preferred salts are the nitrates which are readily available and easily soluble. Optionally, each of the catalytic ingredients may be incorporated by the use of soluble complex salts or compounds with the desired base elements, which upon calcination will yield the desired ratio of the elements in the finished catalyst.

Other variations in starting materials will suggest themselves to those skilled in the art, particularly where preferred starting materials mentioned above are unsuited to the economics of large-scale manufacture. In general, any compound containing the desired catalyst components may be used provided that it results, upon heating to a temperature within the range disclosed hereinafter, in a complex of oxides of the essential catalytic ingredients, which complex upon reduction yields the methanation catalyst of this invention. Proper selection of the proportion of the elements present in the catalyst will influence the selectivity of a particular methanation or gas equilibration reaction. Thus, in some cases one might use a relatively high amount of nickel, and a lower amount of molybdenum, while in other cases one might use lower amounts of nickel.

The catalytic activity of the novel catalyst embodied in the present invention is predicated upon reduction of the complex of oxides with a reducing gas at an elevated temperature. Reduction is generally accomplished with hydrogen, with or without other generally reducing gases. Preferably, the complex of oxides of the catalytic ingredients supported on a suitable catalyst support is heated at a temperature of from about 260°C to about 530°C for from about 2 to 24 hours in a stream of essentially pure hydrogen, The process of the instant invention is specifically concerned with the conversion of carbon monoxide to methane and some ethane. This process comprises passing a mixture of CO and $H_2$ preferably in a molar ratio of about 1:3, in the presence or absence of one or more diluents such as steam, methane and other lower hydrocarbons, carbon dioxide, nitrogen oxides, nitrogen or other inert gas, at relatively high temperature and pressure over the catalyst of the composition described hereinabove. It is preferred that the feed stream be essentially free of hydrocarbons having more than three carbon atoms, though the presence of small quantities of such hydrocarbons including olefins does not appear to affect the methanation adversely. More particularly, the process of this invention is concerned with conversion of carbon monoxide present in an amount in excess of 10 mole percent and as much as 50 mole percent of the volume of the feed gas.

The above described catalyst is active at temperatures in the range from about 400°C to about 625°C, and the preferred range for the methanation reaction is between 500°C and 600°C. In this operating temperature range the catalyst exhibits surprising activity and selectivity, and excellent thermal stability.

The pressure at which the instant process is usually conducted is at elevated pressures in the range from about 300 psig to about 1500 psig, and preferably in the range from about 500 psig to about 1200 psig.

The apparent contact time employed in the instant process may be within the range from about 0.1 to 10 seconds, and for good selectivity and yields a contact time of from about 0.2 to about 5 seconds is preferred.

The molar ratio of $H_2$:CO may vary from about 1:1 to about 10:1 without deleteriously affecting the activity of the catalyst, and without undue deposition of carbon. Ratios below 3 to 1 result in a product mixture of methane and carbon dioxide, while ratios much above 3 to 1 do not appear to provide any economic advantage over a ratio slightly greater than 3. For maximum fraction of methane in the dry product gas, the preferred molar ratio of hydrogen to carbon monoxide is in the range from about 3 to 1 to about 3.5 to 1. Gases such as steam, methane, ethane and carbon dioxide may be present in the feed for process reasons, or to provide a diluent, but for economic reasons, such as equipment sizing and thermal efficiency, the addition of diluent gases is generally avoided.

The reactor employed for the conversion of carbon monoxide and hydrogen to methane in the instant invention may be a fixed bed reactor or a fluid bed reactor. Changes in the physical characteristics of the catalyst described above, particularly to suit either the fluid bed or the fixed bed reactor, may be made according to known methods familiar to those skilled in the art.

For comparison purposes, three methanation catalysts are prepared as in the following examples:

EXAMPLE 1

Supported nickel-copper-molybdenum catalyst.

Impregnate 1000 g. gamma alumina extrudate or powder such as either Harshaw Al-3105E or Al-3109P supports with about 800 ml. ammonium molybdate solution made by stirring 125 g. $MoO_3$ into 125 g. of 26 Baume $NH_4OH$, plus sufficient water to make up the remaining volume.

After the powder is dried for 16 hours at about 120°C and calcined in air at about 499°C for one hour, the composition is about 11.1% $MoO_3$ on alumina.

Take 100 g. of the supported $MoO_3$ so prepared and impregnate it with 75 ml. of an aqueous solution of 22 g. nickel nitrate $Ni(NO_3)_2 \cdot 6H_2O$ and 17 g. copper nitrate $Cu(NO_3)_2 \cdot 3H_2O$. The impregnated supported $MoO_3$ is dried for 16 hours at 120°C and calcined in air for about one hour at 520°C to yield a complex of 5% NiO, 5% CuO, and 10% $MoO_3$ supported on alumina.

EXAMPLE 2

Supported nickel-copper catalyst.

Impregnate 100 g. gamma alumina powder of either type mentioned in Example 1 hereinabove, with a sufficient quantity of an aqueous solution of nickel nitrate and copper nitrate to yield 5% NiO and 5% CuO the finished oxidized catalyst. The impregnated support is dried for 16 hours at 120°C and then calcined in air for one hour at 520°C to yield a complex of nickel and copper oxides supported on gamma alumina.

EXAMPLE 3

Supported molybdenum catalyst.

Impregnate 100 g. gamma alumina powder as described in the first two paragraphs of Example 1 hereinabove, to yield 11.1% $MoO_3$ on the support.

EXAMPLES 4–6

Each of the supported methanation catalyst prepared in Examples 1 to 3 hereinabove is evaluated in a tubular fixed bed reactor having a bed volume of 10 cc. After each supported catalyst is charged to the reactor, hydrogen gas at 400°C is flowed through the catalyst bed for 24 hours to reduce the complex of oxides. Where only $MoO_3$ is present on the support it is to be expected that the effect of reduction under these conditions is not substantial.

The reactor is maintained at 438°C and 1000 psig. The composition of the feed gas, which is kept constant, analyzes 60% $H_2$, 20% CO and 20% $CH_4$. The feed gas is introduced into the reactor at a space velocity of about 1000 $hr^{-1}$.* Product gases from the reactor are dried to remove only moisture and then analyzed with gas chromatographic means. Results of the tests are summarized in the following table wherein conversion is calculated and stated as percentage of initial carbon monoxide reacted.

TABLE I

COMPARATIVE PERFORMANCE TEST DATA

| EX. | CATALYST | CONVERSION % after 100 hrs | $C_2/C_1$ in product | %CO converted to $C_2H_6$ |
|---|---|---|---|---|
| 4 | Ni—Cu—Mo | 85 | 0.04 | 3.3 |
| 5 | Ni—Cu | 80 | 0.003 | 0.2 |
| 6 | Mo | 60 | 0.08 | 4.4 |

* S.V. defined as volumes of gas at standard temperature and pressure, per volume of catalyst, per hour.

The foregoing results indicate that, after 100 hours, conversion of the novel NiCuMo catalyst is substantially greater than Mo alone. Since the combined action of the catalyst ingredients is greater than the sum of the two effects, namely of Ni-Cu and Mo taken independently, synergism is demonstrated. Of greatest interest is the surprising evidence that Ni-Cu-Mo has far superior capacity, compared with Ni-Cu, to make ethane, and slightly higher activity than Ni-Cu. Also, Ni-Cu-Mo has much higher activity than Mo, although Mo makes more ethane.

It is further noted that the methanation at high pressures with the CiCuMo catalyst results in essentially no carbon deposition on the catalyst. Comparable results are obtained where (a) nickel oxide is present, prior to activation, in the range from about 5 to about 40 percent by weight of finished supported catalyst, and the ratio of NiO to CuO is in the range from about 1 to about 9, but more preferably in the range from about 1 to about 3; and, (b) molybdenum oxide is present, prior to activation, in the range from about 5 to about 20 percent by weight of finished supported catalyst, and the ratio of nickel oxide to molybdenum oxide is in the range from about 0.5 to about 5, but more preferably in the range from about 0.5 to about 2.0.

Additional examples of methanation catalyst are prepared to determine the long term characteristics of the catalysts attributable to nickel alone, molybdenum alone, and the combination of nickel and molybdenum.

EXAMPLE 7

Precipitated gamma alumina is slurried with sufficient ammonium molybdate solution to yield 12.4% $MoO_3$ on the finished oxidized catalyst. The slurry is spray dried in a conventional manner, dried at 120°C and calcined in air at 593°C for about one hour to yield $MoO_3$ supported on gamma alumina.

EXAMPLE 8

A portion of the calcined catalyst obtained as described in Example 7 hereinabove is impregnated with an aqueous solution of nickel nitrate so as to yield 5% NiO on the finished oxidized catalyst. The impregnated catalyst is dried at 120°C and calcined in air at 593°C for about one hour to yield a complex of nickel oxide and molybdenum oxide supported on gamma alumina.

EXAMPLE 9

Gamma alumina powder is impregnated with a sufficient quantity of aqueous nickel nitrate to yield 5% NiO on the finished oxidized catalyst. The impregnated catalyst is dried at 120°C and calcined in air at 540°C for about one hour, to yield nickel oxide supported on gamma alumina.

10–12

Each of the supported methanation catalysts prepared in Examples 7 to 9 hereinabove is evaluated in a tubular fixed bed reactor having a bed volume of 10 cc. After each catalyst is charged to the reactor, hydrogen gas at 400°C is flowed through the catalyst bed for 24 hours. The composition of the feed gas, which is kept essentially constant, analyzes 75% $H_2$ and 25% CO. The reactor is maintained at 455°C and 1000 psig and feed rate to the reactor is set for a space velocity of 1200 hr116 [1.] Product gases from the reactor are dried to remove only moisture and then analyzed with gas chromatographic means.

Results of the tests are summarized in the following table wherein conversion is calculated and stated as percentage of initial carbon monoxide reacted.

TABLE II

COMPARATIVE PERFORMANCE TEST DATA

| EXAMPLES | CATALYST | CONVERSION OF CO |
|---|---|---|
| 10 | Mo | about 60% maintained steady for duration of 400 hour run. |
| 11 | Ni | nearly 100% during first three hours, declining to less than 10% in 72 hours. |
| 12 | Ni-Mo | about 80–100% during first three hours, declining steadily to about 60% by 300 hours, and is maintained steady for an additional 100 hours. |

It is clear from the foregoing results that supported, reduced nickel oxide alone decays rapidly after an initial high conversion. The supported, reduced molybdenum oxide alone displays a steady activity level at a generally unacceptable conversion. The reduced combined oxides of nickel and molybdenum indicate that the initial high conversion of CO cannot be maintained. The presence of Cu is critical to provide the stability without which the contribution of nickel declines at an unacceptable rate, such that the Ni-Mo catalyst is approximately equivalent to Mo alone for practical purposes.

Comparable results, indicating the critical stabilizing contribution of Cu, are obtained where (a) nickel oxide is present, prior to activation, in the range from about 5 to about 40 percent by weight of finished supported catalyst, and, (b) molybdenum oxide is present, prior to activation, in the range from about 5 to about 20 percent by weight of finished supported catalyst, and the ratio of nickel oxide to molybdenum oxide is in the range from about 0.2 to about 5, but more preferably in the range from about 0.5 to about 2.

EXAMPLE 13

A nickel-copper-molybdenum methanation catalyst is prepared in a manner analogous to that described in Example 1 hereinabove, utilizing component quantities sufficient to yield a finished calcined catalyst with 8.2% nickel oxide, 3.0% copper oxide and 9.5% molybdenum oxide present as a complex of essential catalytic ingredients.

The Ni-Cu-Mo catalyst is charged to a fluid bed reactor equipped with internal heat removal means. The catalyst is activated by flowing $H_2$ at 400°C through the bed for 24 hours. The reactor is maintained at 482°C and about 1000 psig. Feed gas composition to the reactor analyzes 48% $H_2$, 27% CO, 10.0% $CO_2$ and 15% $CH_4$. Feed gas to the reactor is maintained steady for a space velocity of 1600 $hrs^{-1}$.

Conversion, calculated as before, is 95 mole percent and no decline in conversion is observed at the end of a four-day run. There is no visible carbon formation in the reactor.

In an analogous manner catalysts are prepared having a weight ratio of NiO/CuO as high as 9, but preferably less than about 3, which display highly stable catalytic activity with an excess of 80 mole percent conversion to methane. Steady activity with essentially no carbon deposition is maintained with relatively low ratio of $H_2$ to CO in the feed, for example $H_2$/CO of about 1.73, and as low as 1.

Similar results to those described hereinabove are obtained with a fixed bed reactor.

EXAMPLE 14

A Ni-Cu-Mo catalyst is prepared in a manner analogous to that described in Example 1 except that sufficient quantities of components are used to yield a finished calcined complex of oxides having 13.0% nickel oxide, 4.3% copper oxide and 9.6% molybdenum oxide. The catalyst powder is extruded to about 0.06 in. diameter and charged to a fixed bed reactor with a 30cc. bed volume. As before, the catalyst charge is activated by flowing $H_2$ gas through the bed at 400°C for 24 hours. Inlet temperature of feed is 400°C and feed composition is 80% $H_2$, 20% CO. Reactor pressure and space velocity are maintained steady at 600 psig and 4800 $hr^{-1}$ respectively.

During the run, temperatures as high as 625°C are registered by an axial thermowell near the center of the bed, with no apparent loss of stability in activity. Conversion of 86–88% is observed during a 30-hour period with no noticeable decline. Thereafter flow rates were varied over an additional period of 140 hours, and the above-stated process conditions reestablished. A conversion of 86–88% is again observed. After completion of the run examination of the interior of the reactor indicates an absence of carbon deposition. If, for any reason, carbon deposition does occur, with a resulting loss in activity, the Ni-CU-Mo catalyst is easily regenerated and its original activity is restored.

From the foregoing description and the examples, it will be apparent that acceptable methanation performance of the reduced catalytic complex of oxides of nickel, copper and molybdenum may be obtained over a relatively wide range of ratios of the particular catalytic components, but optimum performance is realized where, prior to activation, nickel oxide and molybdenum oxide are present in the range from 5 to 40 percent, and 5 to 20 percent respectively, by weight of finished supported catalyst; and, further where the weight ratios of nickel oxide to copper oxide is in the range from 1 to 3. The presence of the essential catalytic ingredients in proportions outside these specified proportions may give a usable catalyst, but with no substantial advantage.

Those skilled in the art will recognize that the methanation process of this invention is not necessarily the final step in preparing an acceptable pipeline gas. Accordingly, it is suggested that the instant process be utilized as a precursor processing step to methanate a sufficiently high fraction of feed so as to facilitate the finishing of the predominantly methane-containing product gas, on a moisture-free basis, with any known finishing methanation catalyst. By "finishing methanation catalyst" we refer to a catalyst especially suitable for the methanation of a predominantly methane-containing feed having a relatively low fraction of carbon monoxide, less than 5 percent by volume, such that essentially all the carbon monoxide in the feed is converted to methane. A typical finishing methanation catalyst consists essentially of supported nickel, present prior to activation, in the range from about 5 to about 60 percent by weight of supported catalyst.

It will also be recognized, that, depending upon the particular process conditions and composition of the instant NiCuMo catalyst chosen for primary methanation prior to a finishing step, it may be desirable to adjust the composition and temperature of the effluent from the primary methanation step. For example, it may be desirable to cool the effluent sufficiently to accommodate the exothermic reaction over the finishing methanation catalyst. Again, depending upon the sensitivity of the finishing methanation catalyst chosen, it may be desirable to remove at least some of either the water or the carbon dioxide in the effluent, or both.

Modifications, changes, and improvements to the preferred forms of the invention herein disclosed, described, and illustrated may occur to those skilled in the art who come to understand the principles and precepts thereof. Accordingly, the scope of the patent to be issued hereon should not be limited to the particular embodiments of the invention set forth herein, but rather should be limited by the advance by which the invention has promoted the art.

1. A supported methanation catalyst for the production of gaseous hydrocarbon mixtures, composed predominantly of methane with up to about 5 percent of ethane, on a moisture-free basis, said catalyst prepared by reduction with hydrogen of a complex of oxides on a catalyst support, said complex defined by the formula $Ni_aCu_bMo_cO_x$, wherein a, b and c are numbers so chosen that when b is unity, a and c are in the range from about 1 to about 9, and x is a number determined by the valence requirements of the other elements present, wherein the support comprises at least 50 percent of the total weight of the catalyst, the remainder including from about 5% to about 20% by weight of molybdenum oxide, based on total catalyst, from about 5% to about 40% by weight of nickel oxide, and copper oxide, wherein the weight ratio of the nickel oxide to the copper oxide is in the range from about 1:1 and 9:1.

2. The supported catalyst of claim 1 wherein the support is present in an amount from about 70% to about 95% by weight of the finished catalyst.

3. The supported catalyst of claim 1 wherein the weeight ratio of nickel oxide ot molybdenum oxide is between 0.2 and 5.

* * * * *

UNITED STATES PATENT OFFICE
CERTIFICATE OF CORRECTION

PATENT NO. : 3,962,140
DATED : June 8, 1976
INVENTOR(S) : William R. Alcorn and Leonard A. Cullo It is certified that error appears in the above-identified patent and that said Letters Patent are hereby corrected as shown below:

Column 10, line 34, "Ci" should be "Ni".

Column 12, line 52, "CU" should be "Cu".

Column 11, line 21, "1200 hr 116!" should be "1200 hr.$^{-1}$"

Column 14, line 30, "weeight" should be "weight"

Column 14, line 30, "ot" should be "to"

Column 14, line 15, "$Ni_a Cu_b Mo_c O x$" should be "$Ni_a Cu_b Mo_c O_x$"

Signed and Sealed this

Fourth Day of October 1977

[SEAL]

Attest:

RUTH C. MASON
Attesting Officer

LUTRELLE F. PARKER
Acting Commissioner of Patents and Trademarks